(12) United States Patent
Zhang

(10) Patent No.: US 9,751,863 B2
(45) Date of Patent: Sep. 5, 2017

(54) THERAPEUTICALLY ACTIVE COMPOUNDS AND THEIR METHODS OF USE

(71) Applicant: Agios Pharmaceuticals, Inc., Cambridge, MA (US)

(72) Inventor: Shijie Zhang, Nashua, NH (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/229,011

(22) Filed: Aug. 4, 2016

(65) Prior Publication Data

US 2017/0037031 A1 Feb. 9, 2017

Related U.S. Application Data

(60) Provisional application No. 62/201,546, filed on Aug. 5, 2015.

(51) Int. Cl.

| C07D 401/04 | (2006.01) |
|---|---|
| C07D 401/12 | (2006.01) |
| C07D 401/14 | (2006.01) |
| C07D 403/04 | (2006.01) |
| C07D 403/12 | (2006.01) |
| C07D 403/14 | (2006.01) |

(52) U.S. Cl.
CPC ......... *C07D 401/14* (2013.01); *C07D 401/04* (2013.01); *C07D 401/12* (2013.01)

(58) Field of Classification Search
CPC .. C07D 251/30; C07D 251/48; C07D 401/04; C07D 401/12; C07D 401/14; C07D 403/04; C07D 403/12; C07D 403/14
USPC ................. 544/220, 217, 209, 208
See application file for complete search history.

(56) References Cited

U.S. PATENT DOCUMENTS

| 2,390,529 A | 12/1945 | Friedheim | |
|---|---|---|---|
| 6,274,620 B1 | 8/2001 | Labrecque et al. | |
| 9,512,107 B2 * | 12/2016 | Cianchetta | A61K 31/5377 |
| 2010/0129350 A1 | 5/2010 | Zacharie et al. | |
| 2012/0238576 A1 | 9/2012 | Tao et al. | |
| 2013/0190287 A1 | 7/2013 | Cianchetta et al. | |
| 2015/0018328 A1 * | 1/2015 | Konteatis | C07D 417/04 |
| | | | 514/210.2 |
| 2016/0089374 A1 | 3/2016 | Agresta | |
| 2016/0158241 A1 | 6/2016 | Travins et al. | |
| 2016/0194305 A1 | 7/2016 | Agresta et al. | |

FOREIGN PATENT DOCUMENTS

| DE | 3314663 | 10/1983 |
|---|---|---|
| DE | 3512630 | 10/1986 |
| EP | 0 466 647 | 1/1992 |
| JP | 11158073 A | 6/1999 |
| WO | 2004009562 | 1/2004 |
| WO | 2008131547 | 11/2008 |
| WO | 2009118567 | 10/2009 |
| WO | 2010144338 | 12/2010 |
| WO | 2013102431 | 7/2013 |
| WO | 2013133367 | 9/2013 |
| WO | 2015017821 | 2/2015 |
| WO | 2016126798 | 8/2016 |

OTHER PUBLICATIONS

Hu et al., Bull. Chem. Soc. Ethiop. 2010, 24(3), 425-432.*
Ansell et al. "The interactions of artificial coenzymes with alcohol dehydrogenase and other NAD(P)(H) dependent enzymes" Journal of Molecular Catalysis B: Enzymatic, 6(1-2):111-123 (1999).
Berge et al., "Pharmaceutically Acceptable Salts" J. Pharm. Sci., 66(1):1-19 (1977).
Chan et al. "Multi-domain hydrogen-bond forming metal chelates: X-ray crystal structures of dicyclopalladated 2,3-bis [6-(2-amino-4-phenylamino-1,3,5-triazinyl)]pyrazine (H2L) [Pd2Br2L] and 2,6-bis[6-(2-amino-4-phenylamino-1,3,5-triazinylium)]—pyridine dichloride" Chemical Communications, 1:81-83 (1996).
Dang et al., "Cancer-associated IDH1 mutations produce 2-hydroxyglutarate," Nature, 462:739-744 (2009).
Final office action for U.S. Appl. No. 13/735,467 dated Dec. 3, 2015 (15 pages).
Gerhard et al., Genome Res. 14:2121 2127(2004).
International Search Report for PCT/CN2013/000009 dated Mar. 24, 2013 (6 pages).
International Search Report for PCT/US2014/046204 dated Sep. 15, 2014 (6 pages).
International Search Report for PCT/US2014/049469 dated Jan. 6, 2015 (5 pages).
Kelarev et al. "Synthesis and properties of sym-triazines. 10 Synthesis of 2,4-diamino-sym-triazines containing a sterically hindered phenol substituent" Chemistry of Heterocyclic Compounds, 28(10):1189-1193 (1992).
Koshelev et al. "Synthesis of 1-3,7 N-substituted 2,4-diamino-1,3,5-triazines containing pyridyl groups" Russian Journal of Organic Chemistry, 31(2):260-263 (1995).
Non final office action for U.S. Appl. No. 13/735,467 dated May 22, 2015 (17 pages).
Non final office action for U.S. Appl. No. 14/909,451 dated Aug. 8, 2016 (9 pages).
Supplemental European Search Report for EP 13 73 3752 dated Jul. 20, 2015 (7 pages).
Wang et al., "A novel ligand N,N'-di(2-pyridyl)-2,4-diamino-6-phenyl-1,3,5-triazine (dpdapt) and its complexes: [Cu (dpdapt)Cl$^2$] and [Cu(dpdapt)(NO$^3$)(H$^2$O)]•NO$^3$•H$^2$O, Polyhedron," 2.2 Synthesis of dpdapt, 25:195-202 (2006).
Advisory Action Before the Filing of an Appeal Brief for U.S. Appl. No. 13/735,467 dated Mar. 22, 2016 (3 pages).
Notice of Allowance for U.S. Appl. No. 15/173,519 dated Aug. 10, 2016 (10 pages).
Notice of Allowance for U.S. Appl. No. 15/173,519 dated Sep. 29, 2016 (12 pages).
Non final office action for U.S. Appl. No. 14/904,032 dated Jun. 14, 2016 (31 pages).
Non final office action for U.S. Appl. No. 14/868,283 dated Oct. 27, 2016 (9 pages).

* cited by examiner

*Primary Examiner* — Venkataraman Balasubramanian
(74) *Attorney, Agent, or Firm* — Jones Day

(57) ABSTRACT

Provided are compounds useful for treating cancer and methods of making the compounds and intermediates described herein.

17 Claims, No Drawings

THERAPEUTICALLY ACTIVE COMPOUNDS AND THEIR METHODS OF USE

This application claims priority from U.S. Application Ser. No. 62/201,546 filed Aug. 5, 2015 which is incorporated herein by reference in its entirety.

BACKGROUND OF INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127(2004).

Non-mutant, e.g., wild type, IDH2 catalyzes the oxidative decarboxylation of isocitrate to α-ketoglutarate (α-KG) thereby reducing NAD$^+$ (NADP$^+$) to NADH (NADPH), e.g., in the forward reaction:

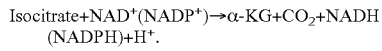

Isocitrate+NAD$^+$(NADP$^+$)→α-KG+CO$_2$+NADH (NADPH)+H$^+$.

It has been discovered that mutations of IDH2 present in certain cancer cells result in a new ability of the enzyme to catalyze the NAPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L et al, Nature 2009, 462:739-44).

The inhibition of mutant IDH2 and its neoactivity is therefore a potential therapeutic treatment for cancer and compounds have been identified that inhibit mutant IDH2 enzyme having the general formula (VIII)

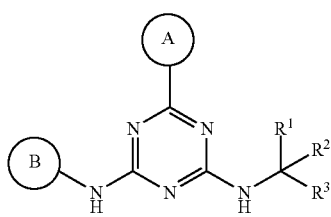

(VIII)

which are described in detail in PCT publication WO2013102431 (incorporated herein by reference in its entirety).

SUMMARY OF INVENTION

Described herein are methods of preparing a compound of formula (I):

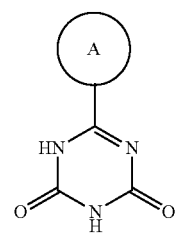

(I)

wherein ring A is an optionally substituted 5-6 member monocyclic aryl or monocyclic heteroaryl, comprising reacting a compound of formula (II):

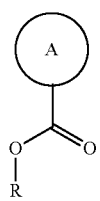

(II)

wherein R is alkyl, alkenyl or alkynyl;
with

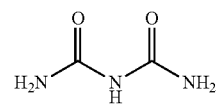

(biuret) in the presence of a dehydrating agent.

In an embodiment, provided herein is a compound of formula (VIb), or a pharmaceutically acceptable salt or hydrate thereof:

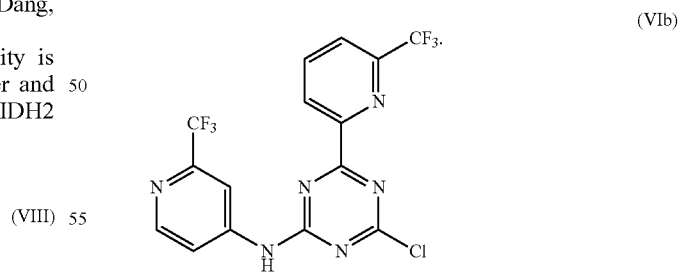

(VIb)

Also provided herein are methods of preparing a compound of formula (VIb), or a pharmaceutically acceptable salt or hydrate thereof.

DETAILED DESCRIPTION

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "aryl" refers to a monovalent monocyclic aromatic group, wherein the aryl is optionally substituted with one or more substituents $Q^1$ as described herein.

The term "heteroaryl" refers to a monovalent monocyclic aromatic group, wherein the aromatic ring contains one or more heteroatoms independently selected from O, S, N, and P in the ring. Heteroaryl groups are bonded to the rest of a molecule through the aromatic ring. The ring of a heteroaryl group can contain one or two O atoms, one or two S atoms, one to four N atoms, and/or one or two P atoms, provided that the total number of heteroatoms in each ring is four or less and each ring contains at least one carbon atom. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In certain embodiments, the heteroaryl is optionally substituted with one or more substituents $Q^1$ as described herein.

The term "heterocycle" or "heterocyclyl" refers to a monocyclic non-aromatic ring system and/or non-aromatic polycyclic ring system, wherein one or more of the non-aromatic ring atoms are heteroatoms, each of which is independently selected from O, S, N, and P; and the remaining ring atoms are carbon atoms. In certain embodiments, the heterocycle has from 3 to 20, from 3 to 15, from 3 to 10, from 3 to 8, from 4 to 7, or from 5 to 6 ring atoms. In certain embodiments, the heterocycle is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated. In certain embodiments, the heterocycle is optionally substituted with one or more substituents $Q^1$ as described herein.

The term "carbocyclyl" refers to a cyclic monovalent hydrocarbon radical, wherein the carbocyclyl is optionally substituted with one or more substituents $Q^1$ as described herein. In one embodiment, carbocyclyl groups may be saturated or unsaturated, and/or spiro, and/or non-spiro, and/or bridged, and/or non-bridged, and/or fused bicyclic groups. In certain embodiments, the carbocyclyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of carbocyclyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1] hexyl, bicyclo[2.2.1]heptyl, decalinyl, and adamantyl.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more substituents $Q^1$, each of which is independently selected from, e.g., (a) oxo (=O), halo, cyano (—CN), and nitro (—NO$_2$), trifluoromethyl (CF$_3$); (b) $C_{1-6}$ alkyl, $C_{2-6}$ alkenyl, $C_{2-6}$ alkynyl, $C_{3-10}$ cycloalkyl, $C_{6-14}$ aryl, $C_{6-14}$ aralkyl, haloalkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$—S(O)R$^a$, —S(O)$_2$R$^a$, —S(O)NR$^b$R$^c$, and -S(O)$_2$NR$^b$R$^c$, wherein each R$^a$, R$^b$, R$^e$, and R$^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^e$ together with the N atom to which they are attached form heteroaryl or heterocyclyl, each of which optionally substituted with one or more, in one embodiment, one, two, three, or four, substituents $Q^a$. As used herein, all groups that can be substituted are "optionally substituted," unless otherwise specified.

Disclosed herein are methods for making a compound of the general structural formula (VIII):

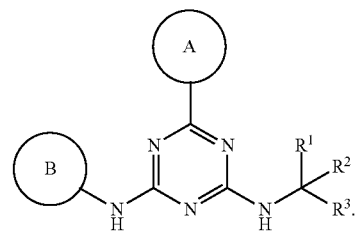

(VIII)

wherein
ring A is an optionally substituted 5-6 member monocyclic aryl or monocyclic heteroaryl;
ring B is an optionally substituted 5-6 member monocyclic aryl or monocyclic heteroaryl;
$R^1$ and $R^3$ are each independently selected from hydrogen, $C_1$-$C_4$ alkyl, $C_1$-$C_4$ haloalkyl, —O—$C_1$-$C_4$ alkyl, and CN, wherein any alkyl portion of $R^1$ is optionally substituted with —OH, NH$_2$, NH($C_1$-$C_4$ alkyl), or N($C_1$-$C_4$ alkyl)$_2$;
$R^2$ is selected from: —($C_1$-$C_6$ alkyl), —($C_2$-$C_6$ alkenyl or alkynyl), —($C_1$-$C_6$ alkylene)-N($R^6$)—($C_1$-$C_6$ alkylene)-O—($C_1$-$C_6$ alkyl), —($C_1$-$C_6$ alkylene)-N($R^6$)—($C_0$-$C_6$ alkylene)-Q, —($C_1$-$C_6$ alkylene)-N($R^6$)($R^6$), —($C_1$-$C_6$ alkylene)-N($R^6$)—S(O)$_{1-2}$—($C_1$-$C_6$ alkyl), —($C_1$-$C_6$ alkylene)-N($R^6$)—S(O)$_{1-2}$—($C_0$-$C_6$ alkyl)-Q, —($C_1$-$C_6$ alkylene)-S(O)$_{1-2}$—N($R^6$)($R^6$), —($C_1$-$C_4$ alkylene)-S(O)$_{1-2}$—N($R^6$)—($C_1$-$C_6$ alkylene)-Q, —C(O)N($R^6$)—($C_1$-$C_6$ alkylene)-C(O)—($C_0$-$C_6$ alkylene)-O—($C_1$-$C_6$ alkyl), —C(O)N($R^6$)—($C_1$-$C_6$ alkylene)-C(O)—($C_0$-$C_6$ alkylene)-O—($C_0$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkyl)-Q, —($C_1$-$C_6$ alkylene)-O—($C_1$-$C_6$ alkyl), —($C_1$-$C_6$ alkylene)-O—($C_1$-$C_6$ alkylene)-Q, —($C_0$-$C_6$ alkylene)-C(O)—($C_0$-$C_6$ alkylene)-O—($C_1$-$C_6$ alkyl), —($C_0$-$C_6$ alkylene)-C(O)—($C_0$-$C_6$ alkylene)-O—($C_1$-$C_6$ alkylene)-Q, —($C_1$-$C_6$ alkylene)-O—C(O)—($C_1$-$C_6$ alkyl), —($C_1$-$C_6$ alkylene)-O—C(O)—($C_0$-$C_6$ alkylene)-Q, —($C_0$-$C_6$ alkylene)-C(O)N($R^6$)—($C_1$-$C_6$ alkyl), —($C_0$-$C_6$ alkylene)-C(O)N($R^6$)—($C_0$-$C_6$ alkylene)-Q, —($C_1$-$C_6$ alkylene)-N($R^6$)C(O)—($C_1$-$C_6$ alkyl), —($C_1$-$C_6$ alkylene)-N($R^6$)C(O)—($C_0$-$C_6$ alkylene)-Q, —($C_0$-$C_6$ alkylene)-S(O)$_{0-2}$—($C_1$-$C_6$ alkyl), —($C_0$-$C_6$ alkylene)-

S(O)$_{0-2}$—(C$_0$-C$_6$ alkylene)-Q, —(C$_1$-C$_6$ alkylene)-N(R$^6$)—C(O)—N(R$^6$)—(C$_1$-C$_6$ alkyl), —(C$_0$-C$_6$ alkylene)-Q, —(C$_0$-C$_6$ alkylene)-C(O)—(C$_1$-C$_6$ alkyl), —(C$_0$-C$_6$ alkylene)-C(O)—(C$_0$-C$_6$ alkylene)-Q, wherein:

any alkyl or alkylene moiety present in R$^2$ is optionally substituted with one or more —OH, —O(C$_1$-C$_4$ alkyl) or halo;

any terminal methyl moiety present in R$^2$ is optionally replaced with —CH$_2$OH, CF$_3$, —CH$_2$F, —CH$_2$Cl, C(O)CH$_3$, C(O)CF$_3$, CN, or CO$_2$H;

each R$^6$ is independently selected from hydrogen and C$_1$-C$_6$ alkyl;

Q is selected from aryl, heteroaryl, carbocyclyl and heterocyclyl, any of which is optionally substituted;

R$^1$ and R$^3$ are optionally taken together with the carbon atom to which they are attached to form C(=O), and R$^1$ and R$^2$ are optionally taken together to form substituted carbocyclyl, optionally substituted heterocyclyl or optionally substituted heteroaryl.

A method for preparing a compound of formula (VIII) comprises reacting a compound of formula (VI)

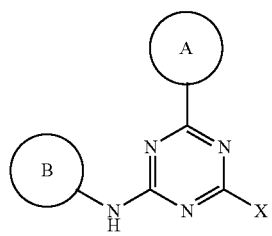

(VI)

wherein rings A and B are as defined herein, with a compound of formula (VII)

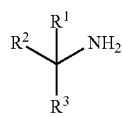

(VII)

wherein X is a leaving group, e.g., halide or a trifluoromethanesulfonate, e.g., X is halide, e.g., X is chloro.

In another embodiment, the methods additionally comprise halogenating a compound of formula (I)

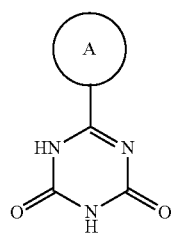

(I)

to give a compound of formula (IV)

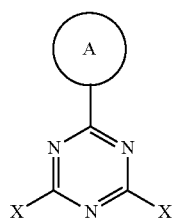

(IV)

wherein X is a leaving group.

In some embodiments, the methods additionally comprise reacting the compound of formula (IV), wherein X is a leaving group, e.g., halide (such as Cl) or a trifluoromethanesulfonate, with a compound of formula (V)

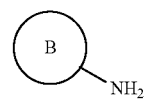

(V)

wherein ring B is as previously defined; to give the compound of formula (VI)

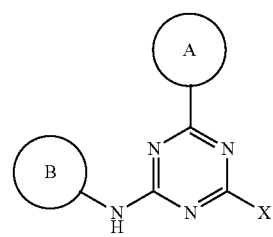

(VI)

In some embodiments, the methods comprise reacting a compound of formula (VI)

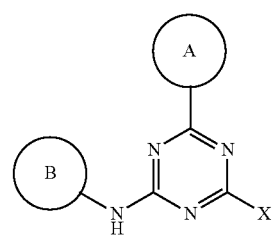

(VI)

with a compound of formula (VII)

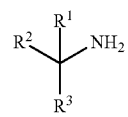

(VII)

wherein R$^1$-R$^3$ are as previously defined to give final compound of formula (VIII).

In an aspect of the invention, there is provided a method of preparing a compound having the formula (I):

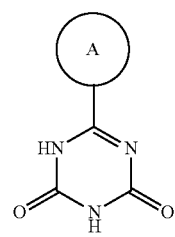

(I)

wherein ring A is as defined above, comprising reacting a compound of formula (II):

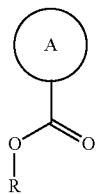

wherein R is alkyl, alkenyl or alkynyl;
with

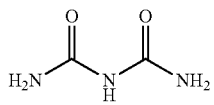

(biuret) in the presence of a dehydrating agent. As demonstrated in the examples herein, the final product is produced in greater yield due to the presence of a dehydrating reagent compared to the analogous reaction without a dehydrating reagent. In an embodiment, the dehydrating reagent comprises trimethyl orthoformate (HC(OMe)$_3$) and trifluoroacetic acid (TFA), e.g., a catalytic amount of TFA. In an embodiment, the dehydrating reagent comprises titanium (IV) ethoxide. In an embodiment, the dehydrating reagent is calcium oxide (CaO). In an embodiment, the dehydrating reagent is magnesium sulfate (MgSO$_4$).

In an embodiment, R is alkyl. In an embodiment, R is methyl. In an embodiment ring A is optionally substituted aryl monocycle. In an embodiment, ring A is an optionally substituted heteroaryl monocycle. In an embodiment, ring A is optionally substituted phenyl. In an embodiment, ring A is phenyl. In an embodiment, ring A is optionally substituted pyridine. In an embodiment, ring A is optionally substituted pyridin-2-yl. In an embodiment, ring A is 6-trifluoromethylpyridin-2-yl.

In an embodiment, the reaction is in the presence of a base comprising an organic or inorganic base. In an embodiment, the base comprises sodium in ethanol, e.g., sodium ethoxide.

In a particular embodiment, there is provided a method of preparing a compound of formula (Ia):

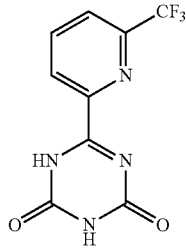

comprising reacting a compound of formula (IIa):

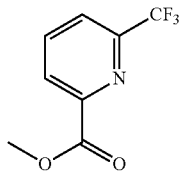

with

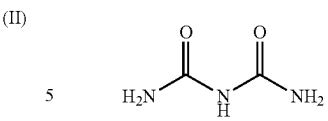

(biuret) in the presence of a dehydrating reagent to provide the compound of formula (IIa). In an embodiment, the dehydrating reagent comprises trimethyl orthoformate (HC(OMe)$_3$) and trifluoroacetic acid (TFA), e.g., a catalytic amount of TFA. In an embodiment, the dehydrating reagent comprises titanium(IV) ethoxide.

In an embodiment, the reaction is in the presence of a base. In an embodiment, the base is sodium ethoxide. In an embodiment, the compound of formula (IIa) is prepared by reacting a compound of formula (IIIa):

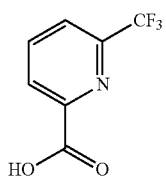

with an acid halide and an alcohol. In one embodiment, the compound of formula (IIa) is prepared by reacting a compound of formula (IIIa) with acetyl chloride and methanol. In an embodiment, the compound of formula (IIa) is prepared by reacting a compound of formula (IIIa) with hydrogen chloride in methanol.

In another aspect of the invention, there is provided a method of preparing a compound of formula (VIIIa):

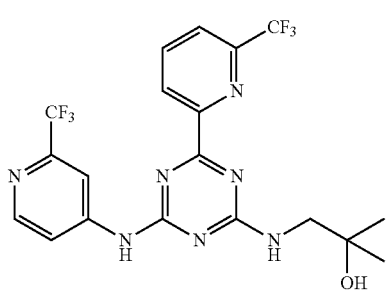

the method comprising reacting a compound of formula (VIa):

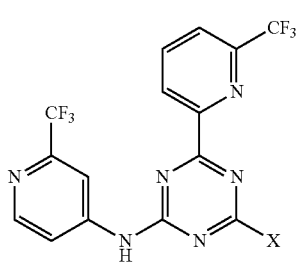

wherein X is a leaving group; with a compound of formula (VIIa):

(VIIa)

H₂N—CH₂—C(CH₃)₂—OH

In an embodiment, X is halide or a trifluoromethanesulfonate. In an embodiment, X is a halide. In an embodiment, X is chloro.

In an embodiment, the reaction occurs in the presence of a base, e.g., an inorganic base. In an embodiment, the base is sodium bicarbonate or potassium phosphate.

In an embodiment, the reaction occurs in the presence of a solvent, e.g., a polar solvent, e.g., a polar aprotic solvent. In an embodiment, the solvent is tetrahydrofuran (THF). In an embodiment, the solvent is 2-methyltetrahydrofuran (2-Me THF).

In an embodiment, the methods comprise preparing the methanesulfonic acid salt of a compound of formula (VIII), wherein:

providing a first solution of methanesulfonic acid in a solvent selected from the group consisting of isopropyl acetate (i-PrOAc), ethyl acetate (EtOAc) and methyl tert-butyl ether (MTBE);

providing a second solution of compound of formula (VIII) in a solvent selected from methyl ethyl ketone (MEK); and combining the first solution and second solutions, to provide the methanesulfonic acid salt of the compound of formula (VIII). In an embodiment, methanesulfonic acid salt of the compound of formula (VIII) is a slurry.

In another embodiment of the invention, there is provided a method of preparing a compound of formula (VIa):

(VIa)

the method comprising reacting a compound of formula (IVa):

(IVa)

wherein X is a leaving group; with a compound of formula (Va):

(Va)

to provide a compound of formula (VIa).

In an embodiment, X is halide or a trifluoromethanesulfonate. In an embodiment, X is halide. In an embodiment, X is chloro.

In an embodiment, the compound of formula (Va) is provided in excess equivalents to the equivalents of the compound of formula (IVa), e.g., in greater than about 1 equivalent, e.g., greater than about 1.5 equivalents, e.g., greater than about 1.75 equivalents, e.g., greater than about 2 equivalents. In an embodiment, the compound of formula (Va) is provided in greater than about 2 equivalents, e.g., about 2.05 equivalents.

In an embodiment, the reaction occurs in the presence of a solvent, e.g., a polar solvent, e.g., a polar aprotic solvent, e.g., tetrahydrofuran (THF) or 2-methyltetrahydrofuran (2-Me THF). In an embodiment, the solvent is a polar aprotic solvent. In an embodiment, the solvent is 2-Me THF.

In an embodiment, the unreacted excess amount of the compound of formula (Va) is isolated as an amine salt, e.g., an amine hydrochloride salt.

In an embodiment, the amine salt of the compound of formula (Va) is neutralized to provide the compound of formula (Va).

In another aspect of the invention, there is provided a compound of formula (VIb):

(VIb)

In another aspect of the invention, there is provided a method of preparing a compound of formula (IVb) having the following structure:

(IVb)

the method comprising reacting a compound of formula (Ia):

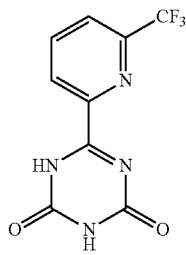

(Ia)

with benzyltriethylammonium chloride (BTEAC) to provide the compound of formula (IVb).

In another embodiment, there is provided a method of preparing a compound of formula (IVb):

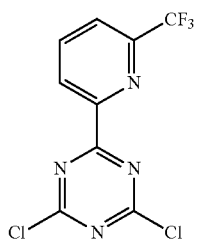

(IVb)

the method comprising contacting a compound of formula (Ia):

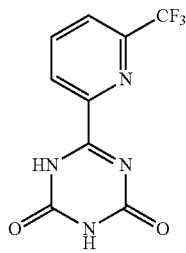

(Ia)

with POCl$_3$ and a base to provide the compound of formula (IVb).

In an embodiment, the base comprises an amine base, e.g., diisopropylethylamine (DIPEA), triethylamine., e.g., DIPEA.

In an embodiment, there is provided a method of preparing a compound of formula (VIIIa)

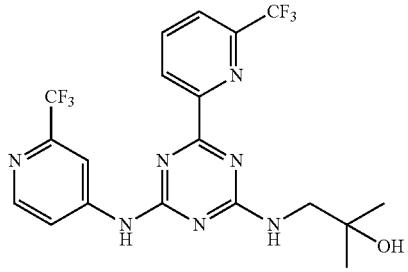

(VIIIa)

comprising a) reacting compound (Ia)

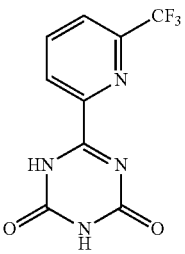

(Ia)

with benzyltriethylammonium chloride and POCl$_3$ to obtain compound (IVb)

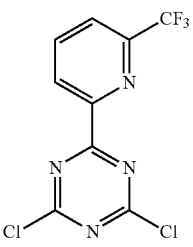

(IVb)

b) reacting compound (IVb) with 2 (trifluoromethyl)pyridin-4-amine to obtain compound (VIb)

(VIb)

and c) reacting compound (VIb) with 1-amino-2-methylpropan-2-ol to obtain the compound of formula (VIIIa). In an embodiment, step a) comprises heating to about 90° C. to about 100° C., or from about 95° C. to about 98° C. In one embodiment, heating in step a) is carried out for about 18 hours. In an embodiment step a) comprises heating to about 95-98° C. for about 18 hours. In an embodiment, step b) comprises aging at about 20° C. for about 3 h and then heating to about 60-65° C. for about 15.5 h. In an embodiment, step b) is conducted in methyltetrahydrofuran. In an embodiment, step c) is conducted at about 20-30° C. In an embodiment, step c) is conducted in presence of diisopropylethylamine. In an embodiment, compound (Ia) is prepared by reacting compound (IIa)

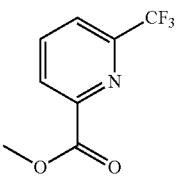

(IIa)

with

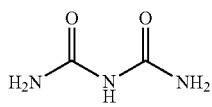

(biuret) in the presence of a dehydrating reagent. In an embodiment, the dehydrating agent comprises trimethyl orthoformate and trifluoroacetic acid. In an embodiment, the dehydrating agent comprises titanium (IV) ethoxide. In an embodiment, the reaction is conducted in the presence of a base. In an embodiment, the base is sodium ethoxide.

The compounds of one aspect of this invention may contain one or more asymmetric centers and thus occur as racemates, racemic mixtures, scalemic mixtures, and diastereomeric mixtures, as well as single enantiomers or individual stereoisomers that are substantially free from another possible enantiomer or stereoisomer. The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%. The term "enriched" means that at least the designated percentage of a preparation is the compound having a selected stereochemistry at one or more selected stereocenters. Methods of obtaining or synthesizing an individual enantiomer or stereoisomer for a given compound are known in the art and may be applied as practicable to final compounds or to starting material or intermediates.

In certain embodiments, the compound of formula (VIII) or any intermediates disclosed herein for preparing the compound of formula (VIII) is enriched for a structure or structures having a selected stereochemistry at one or more carbon atoms. For example, the compound is enriched in the specific stereoisomer by at least about 60%, 65%, 70%, 75%, 80%, 85%, 90%, 95%, 96%, 97%, 98%, or 99%.

The compounds of formula (VIII) or any intermediates disclosed herein for preparing the compound of formula (VIII) may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; N may be in a nay isotopic form, including $^{15}$N; and the like. For example, the compound is enriched in a specific isotopic form of H, C and/or O by at least about 60%, 65%, 70%, 75%, 80%, 85%, 90%, 95%, 96%, 97%, 98%, or 99%.

Unless otherwise indicated when a disclosed compound is named or depicted by a structure without specifying the stereochemistry and has one or more chiral centers, it is understood to represent all possible stereoisomers of the compound.

The compounds described herein may also be represented in multiple tautomeric forms, in such instances, one aspect of the invention expressly includes all tautomeric forms of the compounds described herein, even though only a single tautomeric form may be represented (e.g., alkylation of a ring system may result in alkylation at multiple sites, one aspect of the invention expressly includes all such reaction products; and keto-enol tautomers). All such isomeric forms of such compounds are expressly included herein.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. Sci. Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$ Examples of suitable organic cations include, but are not limited to, ammonium ion (i.e., NH$_4^+$) and substituted ammonium ions (e.g., NH$_3$R$^+$, NH$_2$R$^{2+}$, NHR$^{3+}$, NR$^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Mesylates of each compound in Table 1 are explicitly included herein. Examples of suitable polymeric organic anions include, but are not limited to, those derived from the following polymeric acids: tannic acid, carboxymethyl cellulose.

The compounds provided herein therefore include the compounds themselves, as well as their salts, hydrates and their prodrugs, if applicable. The compounds provided herein may be modified and converted to prodrugs by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine esters), carbamates and other pharmaceutically acceptable derivatives, which, upon administration to a subject, are capable of providing active compounds. Calcium and sodium phosphates of the compounds described herein, if applicable, are explicitly included herein. Amino acid (e.g., valine) esters of the compounds described herein, if applicable, are explicitly included herein.

Compositions and Routes of Administration

The compounds prepared by the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of one aspect of this invention may be administered orally, parenterally, by inhalation spray, topically, rectally, nasally, buccally, vaginally or via an implanted reservoir, preferably by oral administration or administration by injection. The pharmaceutical compositions of one aspect of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of one aspect of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of one aspect of this invention may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of one aspect of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation. Topically-transdermal patches are also included in one aspect of this invention.

The pharmaceutical compositions of one aspect of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of one aspect of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of one aspect of this invention. Alternatively, those agents may be part of a single dosage form, mixed together with the compounds of one aspect of this invention in a single composition.

The compounds prepared by the methods described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of one aspect of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound prepared by the methods described herein, may further comprise another therapeutic agent useful for treating cancer.

Methods of Use

The inhibitory activities of the compounds prepared by the methods described herein can be tested against IDH2 mutants (e.g., IDH2R140Q and IDH2R172K) by methods described in U.S. Ser. No. 13/735,467, Publication No. US/2013/0190287, and International Application No. PCT/US2014/049469, each of which is incorporated herein by reference in its entirety.

The compounds prepared by the methods described herein can be used in inhibiting a mutant IDH2 activity. In one embodiment, the mutant IDH2 has an R140X mutation. In another embodiment, the R140X mutation is a R140Q mutation. In another embodiment, the R140X mutation is a R140W mutation. In another embodiment, the R140X mutation is a R140L mutation. In another embodiment, the mutant IDH2 has an R172X mutation. In another embodiment, the R172X mutation is a R172K mutation. In another embodiment, the R172X mutation is a R172G mutation.

The compounds prepared by the methods described herein can be used in treating a cancer characterized by the presence of a mutant allele of IDH2. In one embodiment, the cancer to be treated is characterized by a mutant allele of IDH2 wherein the IDH2 mutation results in a new ability of the enzyme to catalyze the NAPH-dependent reduction of α-ketoglutarate to R(−)-2-hydroxyglutarate in a patient. In one embodiment, the mutant IDH2 has an R140X mutation. In another embodiment, the R140X mutation is a R140Q mutation. In another embodiment, the R140X mutation is a R140W mutation. In another embodiment, the R140X mutation is a R140L mutation. In another embodiment, the mutant IDH2 has an R172X mutation. In another embodiment, the R172X mutation is a R172K mutation. In another embodiment, the R172X mutation is a R172G mutation. A cancer can be analyzed by sequencing cell samples to determine the presence and specific nature of (e.g., the changed amino acid present at) a mutation at amino acid 140 and/or 172 of IDH2. In an embodiment, the cancer is glioblastoma (glioma), myelodysplastic syndrome (MDS), myeloproliferative neoplasm (MPN), acute myelogenous leukemia (AML), sarcoma, melanoma, non-small cell lung cancer, chondrosarcoma, cholangiocarcinomas or angioimmunoblastic lymphoma.

Without being bound by theory, applicants believe that mutant alleles of IDH2 wherein the IDH2 mutation results in a new ability of the enzyme to catalyze the NAPH-dependent reduction of α-ketoglutarate to R(−)-2-hydroxyglutarate, and in particular R140Q and/or R172K mutations of IDH2, characterize a subset of all types of cancers, without regard to their cellular nature or location in the body. Thus, the compounds prepared by the methods described herein are useful for treating any type of cancer that is characterized by the presence of a mutant allele of IDH2 imparting such activity and in particular an IDH2 R140Q and/or R172K mutation.

Combination Therapies

In some embodiments, the compounds prepared by the methods described herein can be co-administered to a subject in need thereof with a second therapy e.g., an additional cancer therapeutic agent or an additional cancer treatment.

EXAMPLES

Abbreviations
anhy.—anhydrous
aq.—aqueous
min—minute(s)
mL—milliliter
mmol—millimole(s)
mol—mole(s)
MS—mass spectrometry
NMR—nuclear magnetic resonance
TLC—thin layer chromatography
HPLC—high-performance liquid chromatography
Hz—hertz
δ—chemical shift
J—coupling constant
s—singlet
d—doublet
t—triplet
q—quartet
m—multiplet br—broad
qd—quartet of doublets
dquin—doublet of quintets
dd—doublet of doublets
dt—doublet of triplets
CHCl₃—chloroform
DCM—dichloromethane
DMF—dimethylformamide
Et₂O—diethyl ether
EtOH—ethyl alcohol
EtOAc—ethyl acetate
MeOH—methyl alcohol
MeCN—acetonitrile
PE—petroleum ether
THF—tetrahydrofuran
AcOH—acetic acid
HCl—hydrochloric acid
H₂SO₄—sulfuric acid
NH₄Cl—ammonium chloride
KOH—potassium hydroxide
NaOH—sodium hydroxide
K₂CO₃—potassium carbonate
Na₂CO₃—sodium carbonate
TFA—trifluoroacetic acid
Na₂SO₄—sodium sulfate
NaBH₄—sodium borohydride
NaHCO₃—sodium bicarbonate
LiHMDS—lithium hexamethyldisilylamide
NaHMDS—sodium hexamethyldisilylamide
LAH—lithium aluminum hydride
NaBH₄—sodium borohydride
LDA—lithium diisopropylamide
Et₃N—triethylamine
DMAP—4-(dimethylamino)pyridine
DIPEA—N,N-diisopropylethylamine
NH₄OH—ammonium hydroxide
EDCI—1-ethyl-3-(3-dimethylaminopropyl)carbodiimide
HOBt—1-hydroxybenzotriazole
HATU—O-(7-azabenzotriazol-1-yl)-N,N,N',N'-tetramethyluronium
BINAP—2,2'-bis(diphenylphosphanyl)-1,1'-binaphthyl
BTEAC—benzyltriethylammonium chloride In the following examples, reagents were purchased from commercial sources (including Alfa, Acros, Sigma Aldrich, TCI and Shanghai Chemical Reagent Company), and used without further purification. Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were run with electrospray ionization (ESI) from a Waters LCT TOF Mass Spectrometer (Waters, USA).

For exemplary compounds disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%. The chemical name of each of the exemplary compound described below is generated by ChemDraw software.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Example 1

Preparation of Compound of Formula VIIIa

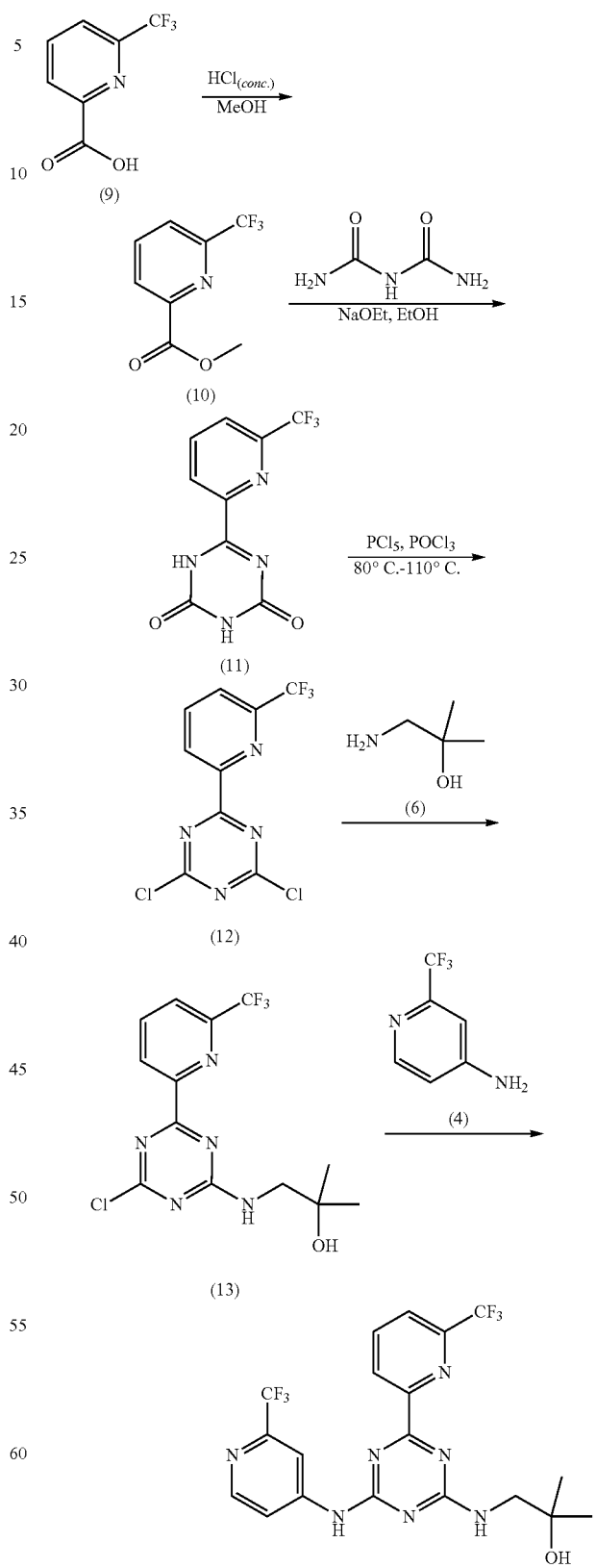

Formual VIIIa 6-trifluoromethyl-pyridine-2-carboxylic acid methyl ester (10).

To a solution of 6-trifluoromethyl-pyridine-2-carboxylic acid in methanol (770 ml) was added concentrated HCl (6 ml). The mixture was stirred at 80° C. for 48 hours then concentrated to remove the volatile. The crude product was diluted with ethyl acetated and washed with Sat. NaHCO$_3$ solution. The organic layer was dried with anhydrous Na$_2$SO$_4$ and concentrated to give 6-trifluoromethyl-pyridine-2-carboxylic acid methyl ester (10) as a white solid. LC-MS: m/z 206 (M+H)$^+$.

6-(6-trifluoromethyl-2-yl)-1,3,5-triazine-2,4-dione (11).

To a solution of Na (32 g, 0.16 mol) in ethanol (500 mL) was added 6-trifluoromethyl-pyridine-2-carboxylic acid methyl ester and biuret (5.3 g, 0.052 mol). The mixture was heated to reflux for 1 hour. Then concentrated to give residue which was poured to water and added Sat.NaHCO$_3$ solution to adjust pH to 7, the precipitated solid was collected by filtration and dried to give 6-(6-trifluoromethylpyridin-2-yl)-1,3,5-triazine-2,4-dione (11) as a pale white solid. LC-MS: m/z 259 (M+H)$^+$.

2,4-dichloro-6-(6-trifluoromethylpyridin-2-yl)-1,3,5-triazine (12).

To a solution of 6-(6-trifluoromethylpyridin-2-yl)-1,3,5-triazine-2,4-dione (11) in POCl$_3$ (48 mL) was added PCl$_5$ (23 g, 0.1 mol). The mixture was stirred at 100° C. for 2 hours then concentrated to remove the volatile. The residue was diluted with ethyl acetated and washed with Sat.NaHCO$_3$ solution. The organic layer was dried over anhydrous Na$_2$SO$_4$ and concentrated to give 2,4-dichloro-6-(6-trifluoromethylpyridin-2-yl)-1,3,5-triazine (12) as a yellow solid. LC-MS: m/z 294.9 (M+H)$^+$.

1-[4-Chloro-6-(6-trifluoromethyl-pyridin-2-yl)-[1,3,5]triazin-2-ylamino]-2-methyl-propan-2-ol (13).

To a solution (12) in anhydrous THF (20 mL) was added 1-amino-2-methylpropan-2-ol. The mixture was stirred at room temperature for 1 hour. The mixture was quenched by water and extracted with ethyl acetate. The organic layer was dried over anhydrous Na$_2$SO$_4$ and concentrated to give 1-[4-chloro-6-(6-trifluoromethyl-pyridin-2-yl)-[1,3,5]triazin-2-ylamino]-2-methyl-propan-2-ol (13) which was used directly in the next step.

2-methyl-1-(4-(6-(trifluoromethyl)pyridin-2-yl)-6-(2-(trifluoromethyl)pyridin-4-ylamino)-1,3,5-triazin-2-ylamino)propan-2-ol (formula VIIIa).

To a solution of 1-[4-chloro-6-(6-trifluoromethyl-pyridin-2-yl)-[1,3,5]triazin-2-ylamino]-2-methyl-propan-2-ol (13) in anhydrous dioxane (3 mL) was added 2-trifluoromethyl-pyridin-4-ylamine (0.13 g, 0.78 mmol), t-BuONa (0.15 g, 1.56 mmol) and Pd(dppf)Cl$_2$ (0.057 g, 0.078 mmol). The mixture was stirred at 80° C. under N$_2$ for 1 hour. The mixture was quenched by water and extracted with ethyl acetate. The organic layer was dried with anhydrous Na$_2$SO$_4$, concentrated and purified by a standard method to give 2-methyl-1-(4-(6-(trifluoromethyl)pyridin-2-yl)-6-(2-(trifluoromethyl)pyridin-4-ylamino)-1,3,5-triazin-2-ylamino)propan-2-ol (formula VIIIa). $^1$H NMR (METHANOL-d$_4$) δ 8.62-8.68 (m, 2 H), 847-8.50 (m, 1 H), 8.18-8.21 (m, 1 H), 7.96-7.98 (m, 1 H), 7.82-7.84 (m, 1 H), 3.56-3.63 (d, J=28 Hz, 2 H), 1.30 (s, 6 H). LC-MS: m/z 474.3 (M+H)$^+$.

Example 2

Preparation of 6-(6-(trifluoromethyl)pyridin-2-yl)-1,3,5-triazine-2,4(1H,3H)-dione

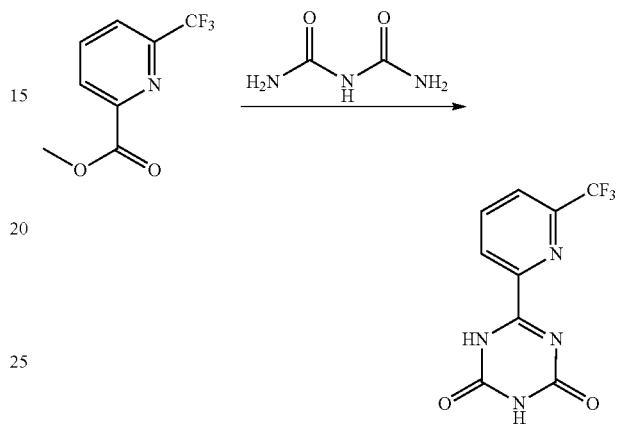

Dry biuret (12.5 g, 122 mmol, 0.5 eq.) was added into NaOEt solution in EtOH (488 mmol, 2.0 eq., premade with 11.2 g Na and 1 L EtOH) at 50-55° C., and stirred for 15 minutes. Methyl 6-(trifluoromethyl)picolinate (50 g, 244 mmol, 1.0 eq.) was added, and the reaction mixture was stirred at 75-80° C. for 2 hours. Concentration of reaction mixture followed by neutralization with concentrated HCl solution generated a slurry. The off-white solid was collected by filtration, washed with water, and dried under vacuum to yield 16 g of product (25% yield).

Example 3

Preparation of 6-(6-(trifluoromethyl)pyridin-2-yl)-1,3,5-triazine-2,4(1H,3H)-dione with Ti(OEt)4 as dehydrating agent

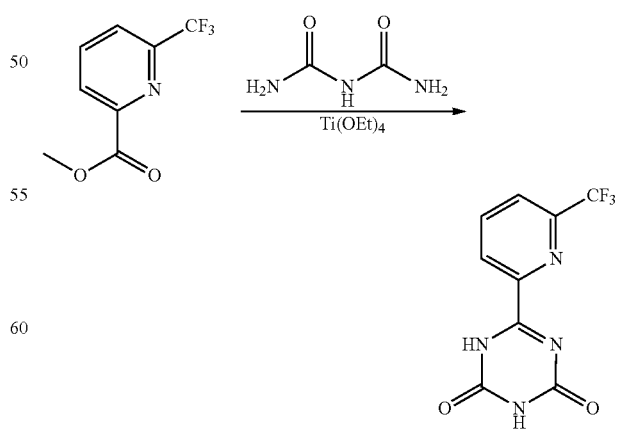

Mixture of methyl 6-(trifluoromethyl)picolinate (50 g, 244 mmol, 1.0 eq.) and biuret (30.2 g, 293 mmol, 1.20 eq.)

in 750 mL EtOH was stirred at 30-35° C. for 10-20 min. Titanium tetraethoxide (Ti(OEt)₄, 27.8 g, 122 mmol, 0.5 eq.) was added and stirred at 30-35° C. for 30-60 min. EtONa solution in EtOH (350 g, 19% wt, 978 mmol, 4.0 eq.) was added, and the reaction mixture was heated at 55-65° C. for 3 hours. The reaction mixture was concentrated, cooled to room temperature, and diluted with 700 mL water. Concentrated HCl solution was added to adjust pH value to pH≤1. Methylene chloride (DCM, 700 mL) was charged, and the slurry was stirred 20-30° C. for 5-7 hours. Solid was collected by filtration, and the cake was sequentially washed twice with 6N HCl, twice with water, and once with DCM. The wet cake was dried at 50-60° C. under vacuum, yielding 6-(6-(trifluoromethyl)pyridin-2-yl)-1,3,5-triazine-2,4(1H,3H)-dione as off-white solid (45.0 g, 174 mmol, 71% yield).

Example 4

Preparation of 6-(6-(trifluoromethyl)pyridin-2-yl)-1,3,5-triazine-2,4(1H,3H)-dione with HC(OMe)₃ and TFA as dehydrating agent

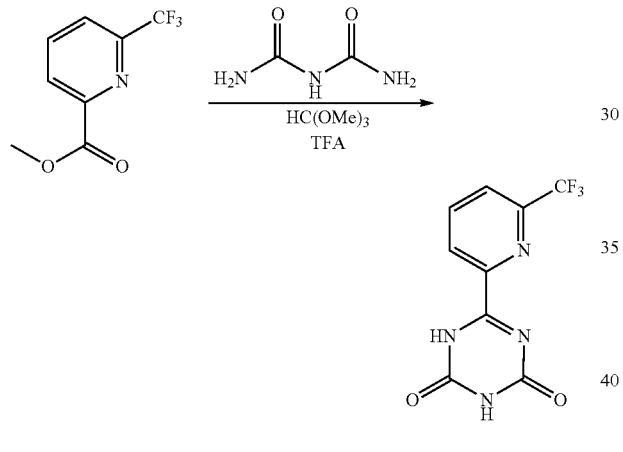

The procedure according to example 2 was performed using 0.6 eq. trimethyl formate (HC(OMe)₃) and 0.05 eq. trifluoroacetic acid (TFA) as dehydrating agent. 57% Isolated yield was obtained for a 200 g scale reaction (200 g of methyl 6-(trifluoromethyl)picolinate).

Example 5

Preparation of 2-methyl-1-((4-(6-(trifluoromethyl)pyridin-2-yl)-6-((2-(trifluoromethyl)pyridin-4-yl)amino)-1,3,5-triazin-2-yl)amino)propan-2-ol (VIIIa)

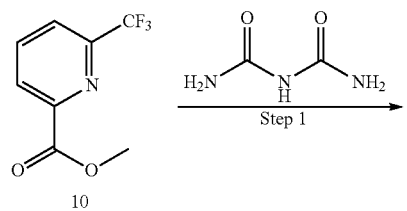

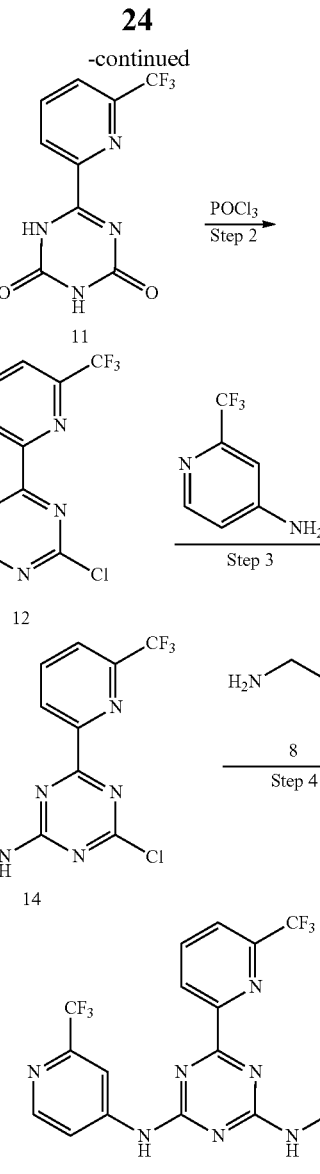

Formual VIIIa

Step 1

A glass reactor (2 L) was charged under nitrogen with compound 10 (0.030 kg, 0.146 mol, 1 eq), Ethanol (0.360 kg, 12 eq) and Biuret (0.018 kg, 0.175 mol, 1.2 eq). The reaction mixture was heated to 30-35° C. and stirred for 10-20 min. Ti(OEt)₄, was charged (0.0168 kg, 0.56 eq). The reaction mixture was heated to 30-35° C. and stirred for 30-60 min. 19% NaOEt solution in EtOH was charged (0.2625 kg, 8.75 eq) over 2 h. The reaction mixture was heated to 55-65° C. over 2 h and stirred for 2-4 h. The reaction mixture was concentrated under vacuum (IT <60° C.) to 0.2 L. The reaction mixture was cooled to 20-30° C. Water (0.450 kg, 15 eq), HCl 35% aqueous solution (0.135 kg, 4.5 eq.), and DCM (0.200 kg, 6.67 eq.). The crude product was aged at 20-30° C. for 5-6 h and then filtered. The crude product was washed with water (0.5-1 eq.). The crude product was charged to water (0.450 kg, 15 eq), NaOH (0.0215 kg, 0.712 eq) and stirred at 20-30° C. for 2-4 h. The crude product was filtered through celite (0.009 kg, 0.3 eq.) and washed with water (0.040 kg, 1.333 eq.). The filtered product was added drop-wise over at least 3 h at 20-30° C. into HCl 35% solution (0.060 kg, 2 eq.) and water (0.225 kg, 7.5 eq.). The product was heated to 20-30° C. and stirred for 1-2 h. The product was filtered, washed with water (6 eq.), and dried under vacuum at 50-70° C. for 20-40 h. Isolated yield: 25.3 g of Compound 11 (67%); HPLC purity 100.0% a/a Step 2

A glass reactor (15 L) was charged under nitrogen with compound 11 (0.892 kg, 3.46 mol, 1 eq), BTEAC (1.970 kg, 8.65 mol, 2.5 eq), and POCl$_3$ (2.150 kg, 14.0 mol, 4.1 eq). The reaction mixture was heated to 95-98° C. for 18 h until reaction completion. The reaction mixture was concentrated under vacuum (IT 82-90° C.) to 3.5 L and then diluted with EtOAc (8.5 kg). The batch was concentrated under reduced pressure to 4 L and then diluted again with EtOAc (2.0 kg). Two additional cycles (dilution followed by concentration) were performed. Finally, the residue was diluted with EtOAc (11.2 kg) when a two-liquid phase mixture resulted. The bottom layer containing BTEAC, some POCl$_3$ and Compound 12 (120 g, 9% of the batch) was separated and discarded.

A 50 L round bottom flask was charged with Na$_2$HPO$_4$ (785 g), NaH$_2$PO$_4$ (1779 g), and water (10.7 L). The phosphate buffer was cooled to 5° C., and the reaction mixture in EtOAc was added slowly over 35 min, while maintaining the IT at 7-10° C. The pH of reaction mixture was 5. The layers were separated. The aqueous layer was extracted with EtOAc (3.44 kg). The combined organic extract was washed with water (3.6 kg) and brine (4.1 kg). The batch was concentrated under reduced pressure to 2 L of residue. The batch was diluted with heptane (5.8 kg) and the mixture was concentrated to (4.4 L). The resulting slurry was treated with heptane (5.8 kg) and concentrated to 4.5 L. The batch was cooled to −3-5° C. for 1 h, and filtered. The product was washed with heptane (2×1.3 L) and dried at 40-45° C. overnight. Isolated yield: 794 g of Compound 12 (78%); HPLC purity 99.2% a/a Step 3

A glass reactor (15 L) was charged under nitrogen with compound 12 (774 g, 2.62 mol, 1 eq) and MeTHF (3.300 kg). The resulting mixture was stirred for 10 min and then 2-(trifluoromethyl)pyridin-4-amine (875 g, 5.40 mol, 2.1 eq) was charged in one portion to the reactor. The reaction mixture was aged at 20° C. for 3 h and then heated to 60-65° C. for 15.5 h until the reaction was complete. The hydrochloride salt of 2-(trifluoromethyl)pyridin-4-amine was removed by filtration, and washed with Me-THF (2×1.060 kg). The combined Me-THF solutions (filtrate+washes) were washed with 0.5 N HCl (2×2 L). The batch was diluted with heptane (1.35 kg) and the resulting yellow solution was washed with water (2×2.1 L). Finally, the organic layer was washed with brine (0.6 kg) and dried by distillation. The Me-THF/heptane mixture was treated with heptane (2.2 kg) at 31-35° C. Additional heptane (3.69 kg) was charged, and the mixture was concentrated under vacuum to 7.4 L. The mixture was diluted with heptane (2.13 kg), concentrated under vacuum to 7.4 L, and then diluted with heptane (2.13 kg). The batch was aged at 20-22° C. for 2 h. Finally, the product was isolated by filtration, washed with heptane (2×1.1 L) and dried at 35° C. for 22 h. Isolated yield: 1.068 kg of 14 (97%) as light yellow powder. HPLC purity 98.5% a/a, Step 4

To a 15 L glass reactor purged with nitrogen was charged Compound 14 (1.038 kg, 2.47 mol, 1 eq), followed by Me-THF (6.176 kg) and DIEA (0.384 kg, 2.97 mol, 1.2 eq). The resulting mixture was stirred at room temperature and then 1-amino-2-methylpropan-2-ol (0.265 kg, 2.97 mol, 1.2 eq) in Me-THF (2.647 kg) was slowly charged while maintaining 20-30° C. After the reaction was complete, water (2.6 L) and n-heptane (2.076 kg) were added. The mixture was stirred for 20 min., the aqueous layer was removed, water (2.6 L) was added and the pH of the aqueous phase adjusted to 7 using 0.1N HCl. The aqueous layer was removed, and the organic layer was washed with water (2×2.6 L), 4% NaHCO$_3$ (1.1 L), and water (1.15 L). The organic layer was concentrated under vacuum to 3.4 L. Me-THF (4.950 kg) was added, and the mixture was concentrated to 3.4 L. The residue was diluted with Me-THF (4.931 kg). The solution was clarified through a 1.2 t in-line filter. The clarified solution was concentrated to 2.6 L. The residue was heated to 45° C., and then n-heptane (2.599 kg) was added slowly while maintaining 45° C. The batch was seeded with 2-methyl-1-((4-(6-(trifluoromethyl)pyridin-2-yl)-6-((2-(trifluoromethyl)pyridin-4-yl)amino)-1,3,5-triazin-2-yl)amino)propan-2-ol (10 g). n-Heptane (2.599 kg) was added slowly while maintaining 45° C. After 1 h, the batch was cooled down to 20° C. The mixture was stirred at 20° C. for 1 h. The batch was filtered. The solids were washed with n-heptane (2×1 L), and then vacuum-dried at 35° C. in an oven for 20 h. Isolated yield: 1.124 kg of 2-methyl-1-((4-(6-(trifluoromethyl)pyridin-2-yl)-6-((2-(trifluoromethyl)pyridin-4-yl) amino)-1,3,5-triazin-2-yl)amino)propan-2-ol (96%) as a light yellow powder.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method of preparing a compound having the formula (I):

wherein ring A is pyridinyl substituted with trifluoromethyl, comprising reacting a compound of formula (II):

wherein R is alkyl, alkenyl or alkynyl;
with

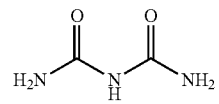

(biuret) in the presence of a dehydrating agent, wherein the dehydrating agent comprises (i) trimethyl orthoformate and a catalytic amount of trifluoroacetic acid or (ii) titanium(IV) ethoxide.

2. A method of preparing a compound of formula (Ia):

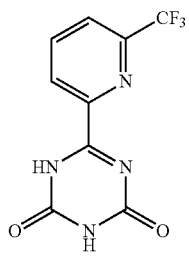

(Ia)

comprising reacting a compound of formula (IIa):

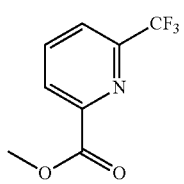

(IIa)

with

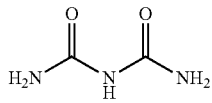

with (biuret) in the presence of a dehydrating reagent to provide the compound of formula (Ia), wherein the dehydrating agent comprises (i) trimethyl orthoformate and a catalytic amount of trifluoroacetic acid or (ii) titanium(IV) ethoxide.

3. The method of claim 2, wherein the reaction is in the presence of a base.

4. The method of claim 3, wherein the base is sodium ethoxide.

5. The method of claim 1, wherein the compound of formula (II) is prepared by reacting a compound of formula (III)

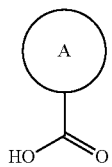

(III)

with an acid halide and an alcohol.

6. The method of claim 2, wherein the compound of formula (IIa) is prepared by reacting a compound of formula (IIIa):

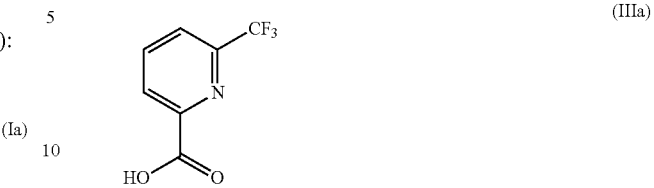

(IIIa)

with hydrogen chloride and methanol.

7. The method of claim 1, further comprising halogenating the compound of formula (I) to give a compound of formula (IV)

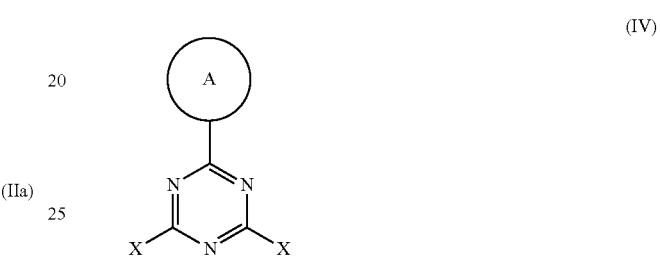

(IV)

wherein X is a halogen.

8. The method of claim 2, further comprising reacting the compound of formula (Ia) with benzyltriethylammonium chloride and $POCl_3$ to give a compound of formula (IVb)

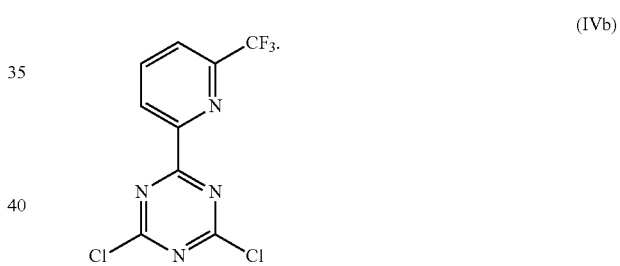

(IVb)

9. The method of claim 8, further comprising reacting the compound of formula (IVb) with a compound of formula (Va)

(Va)

to give a compound of formula (VIb)

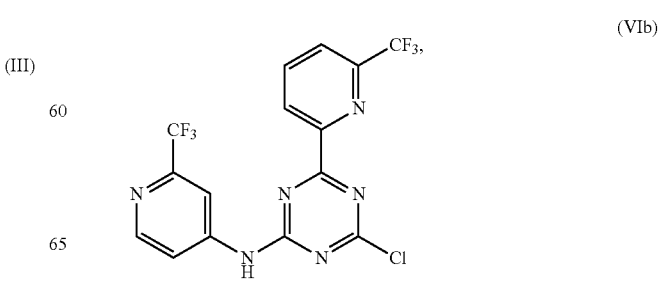

(VIb)

10. A method of preparing a compound of formula (VIIIa)

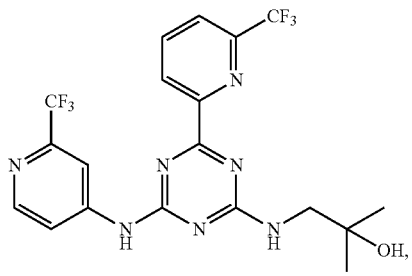
(VIIIa)

comprising a) reacting compound (Ia)

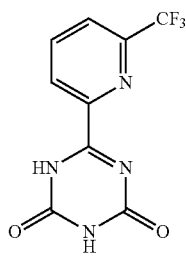
(Ia)

with benzyltriethylammonium chloride and POCl₃ to obtain compound (IVb)

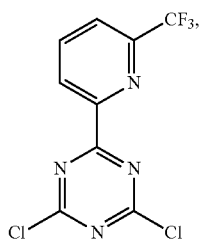
(IVb)

b) reacting compound (IVb) with 2-(trifluoromethyl)pyridin-4-amine to obtain compound (VIb)

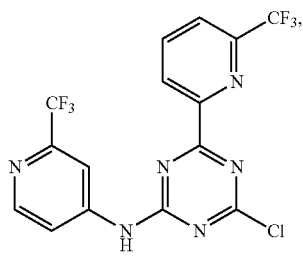
(VIb)

and c) reacting compound (VIb) with 1-amino-2-methylpropan-2-ol to obtain the compound of formula (VIIIa), wherein compound (Ia) is prepared by reacting

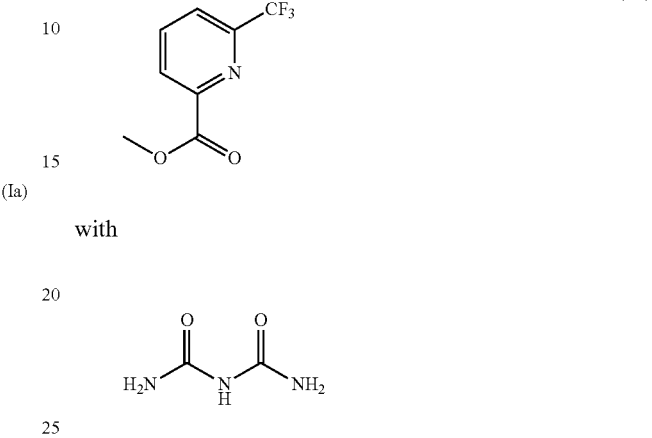
(IIa)

with in the presence of a dehydrating reagent, wherein the dehydrating agent comprises (i) trimethyl orthoformate and a catalytic amount of trifluoroacetic acid or (ii) titanium(IV) ethoxide.

11. The method of claim 10, wherein step a) comprises heating to about 95-98° C. for about 18 hours.

12. The method of claim 10, wherein step b) comprises aging at about 20° C. for about 3 h and then heating to about 60-65° C. for about 15.5 h.

13. The method of claim 10, wherein step b) is conducted in methyltetrahydrofuran.

14. The method of claim 10, wherein step c) is conducted at about 20-30° C.

15. The method of claim 10, wherein step c) is conducted in presence of diisopropylethylamine.

16. The method of claim 10, wherein the reaction of (IIa) is conducted in the presence of a base.

17. The method of claim 16, wherein the base is sodium ethoxide.

* * * * *